United States Patent [19]

Login et al.

[11] Patent Number: 4,987,210
[45] Date of Patent: Jan. 22, 1991

[54] POLYMERIZABLE DERIVATIVES OF 5-OXO-PYRROLIDINECARBOXYLIC ACID

[75] Inventors: Robert B. Login, Oakland; John J. Merianos, Middletown; Gary Dandreaux, Bloomfield; Jenn S. Shih, Paramus, all of N.J.

[73] Assignee: GAF Chemicals Corporation, Wayne, N.J.

[21] Appl. No.: 465,292

[22] Filed: Jan. 16, 1990

Related U.S. Application Data

[62] Division of Ser. No. 266,183, Nov. 3, 1988, Pat. No. 4,946,967.

[51] Int. Cl.$^5$ .............................................. C08F 26/06
[52] U.S. Cl. ........................................................ 526/258
[58] Field of Search ......................................... 526/258

*Primary Examiner*—Joseph L. Schofer
*Assistant Examiner*—Alex H. Walker
*Attorney, Agent, or Firm*—Marilyn J. Maue; Joshua J. Ward

[57] ABSTRACT

The invention relates to 5-oxo-3-pyrrolidinecarboxylic acid derivatives having the structural formula

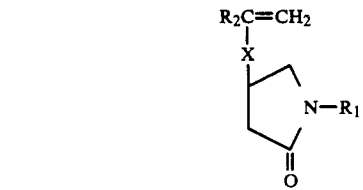

wherein X is selected from the group of

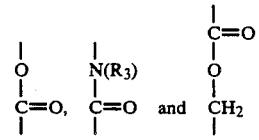

$R_2$ and $R_3$ are each H or $CH_3$, and $R_1$ is H or a hydrocarbon radical having from 1 to 20 carbon atoms, which derivative compounds are suitable as monomers which can be homopolymerized or copolymerized to yield high molecular weight materials having many useful properties and applications, among which is their ability to form complexes with water insoluble molecules which are normally not complexible with similar type polymers.

8 Claims, No Drawings

POLYMERIZABLE DERIVATIVES OF 5-OXO-PYRROLIDINECARBOXYLIC ACID

This is a division of application Ser. No. 266,183, filed Nov. 3, 1988 now U.S. Pat. No. 4,946,967.

BACKGROUND OF THE INVENTION

Polyvinylpyrrolidone (PVP) is a well known synthetic polymer having properties which make it suitable for many pharmaceutical, cosmetic, clinical and industrial uses and applications. One of its most important properties is its ability to form complexes with a large variety of compounds, such as iodine, phenolic materials, and dyes.

The PVP polymer has a linear hydrophobic hydrocarbon backbone wherein every alternate carbon atom is bonded to the nitrogen atom of the carboimide group of the hydrophilic 2-pyrrolidone ring as illustrated by the structural formula

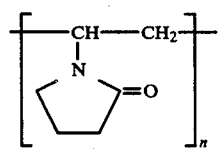

The unique balance between the hydrophobic and hydrophilic segments of the polymer accounts for its unique characteristics. The carboimide moiety of the pyrrolidone is a polarizable group which makes the lactam eminently susceptible to hydrogen bonding and complex formation. There is also evidence that the hydrophobic backbone participates in various types of attractive forces, such as van der Waals forces, which also participate in complex formation. In addition, the pyrrolidone ring complexes with unsaturated hydrocarbons such as substituted or unsubstituted benzene naphthalene, anisole, methyl salicylate, etc., through a charge-transfer system.

Although the complexes of PVP are stable, the intensity of attractive forces between the PVP polymer and other molecules, such as iodine and phenolics, depends to a large extent on the steric properties surrounding the sites where such forces exist. Steric crowding, between the pyrrolidone lactam ring and the hydrocarbon backbone alter the intensity of attractive forces, and lower the stability of the complex. An examination of the structure of polyvinylpyrrolidone shows that steric crowding exists between the amide functional group of the lactam and the hydrocarbon backbone. This is due to the fact that the polymer is derived from vinylpyrrolidone monomer and the hydrocarbon backbone is bonded directly to the nitrogen atom of the lactam ring. Because of this crowding effect, certain molecules having a bulky nature fail to complex, or exibit limited complexing, along the PVP chain.

Accordingly, it is an object of this invention to provide lactam monomers which have considerably reduced steric hindrance between the lactam amide and the hydrocarbon backbone in polymers formed therefrom.

It is another object of this invention to produce a polymer of the present compounds which are capable of complexing with a wide variety of molecules, including molecules having a bulky structure.

Still another object of the invention is to provide a compound which is highly reactive as an intermediate for the formation of numerous addition products.

Yet another object of the invention is to provide a process for the homopolymerization and copolymerization of the present compounds by a commercially feasible and economical process.

These and other objects of the invention will become apparent from the following description and disclosure.

THE INVENTION

It has now been found that a signficant reduction in steric hindrance between the hydrocarbon backbone and the carboimide moiety of a lactam can be achieved by interposing certain groups which do not reduce, but may enhance, the complexing capability of the polymer and which provide a more stable complex.

In accordance with the present invention there is provided a polymerizable compound having the structure

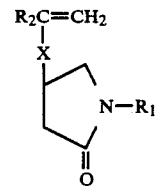

wherein the interposed moiety is represented by X which is selected from the group consisting of

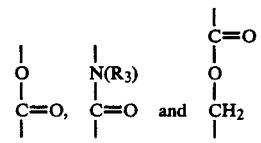

$R_1$ is H or a hydrocarbon radical having from 1 to 20 carbon atoms which includes alkyl, alkenyl, aryl, aralkyl, and alkaryl radicals; and $R_2$ and $R_3$ are each independently hydrogen or methyl.

These compounds are readily halogenated, sulfonated, hydroxylated and oxylated by addition across the double bond to form valuable surfactants, flame retardants and biocides. The present compounds also can be homopolymerized or copolymerized with various co-monomers by commercially feasible and economical processes.

The homopolymers of this invention are characterized by the formula

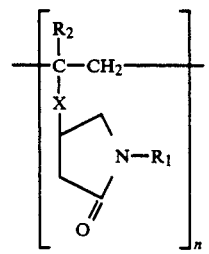

wherein n is an integer having a value of from 10 to 50,000. The above polymeric structure possesses none of the crowding surrounding the sites where attracting forces exist as in the PVP homopolymer defined by the formula

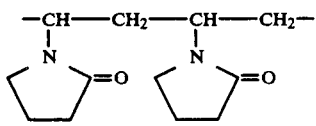

Thus, it becomes apparent that the homopolymers of the present invention possess less steric hindrance between the hydrocarbon backbone and the carboimide function of the lactam ring. The homopolymers of the present invention exist as atactic, syndiotactic or isotactic polymers.

Copolymers of of the present compounds are also economically synthesized in block, graft, random or alternating structure and involve a wide variety of comonomers, examples of which include comonomers containing olefinic unsaturation, quaternary ammonium comonomers and sulfonate comonomers, examples of which are as follows.

Acrylic and Acrylate Comonomers

Acrylic acid, methacrylic acid, methyl methacrylate, methyl acrylate, ethyl methacrylate, 2-ethylhexyl acrylate, butyl methacrylate, lauryl methacrylate, stearyl methacrylate, and other octyl and higher alkyl acrylates, hydroxyethyl acrylate, hydroxypropyl acrylate, hydroxyethyl methacrylate, hydroxypropyl methacrylate, polypropylene glycol monomethacrylate, [(dimethyl amino)ethyl] acrylate, [(diethyl amino)ethyl] acrylate, [(dimethylamino)ethyl]methacrylate, [(diethylamino)ethyl] methacrylate, [(t-butylamino)ethyl] methacrylate, alpha-cyanoacrylate, glycidyl methacrylate, tetrahydrofurfuryl methacrylate, cyclohexyl methacrylate, isobornyl methacrylate, cyclopentenyl methacrylate, ethoxyethyl methacrylate, sulfoethyl methacrylate, allyl methacrylate, methoxyethyl acrylate, ethoxyethyl acrylate, phenoxyethyl acrylate, cyclohexyl acrylate, tetrahydrofurfuryl acrylate, dicyclopentadienyl acrylate, glycidyl acrylate, etc.

Acrylamide and Methacrylamide Comonomers

Acrylamide, N-methylol acrylamide, N-isobutoxymethyl acrylamide, t-butyl and t-octyl acrylamides, 2-acrylamido-2-methylpropane sulfonic acid, methacrylamide, N,N,dimethylacrylamide, [(dimethylamino)propyl] methacrylamide, multifunctional acrylates, tripropylene glycol diacrylate, tetraethylene glycol diacrylate, hexanediol diacrylate, other polyalkylene glycol diacrylates, trimethylolpropane triethoxy triacrylate, glycerol propoxy triacrylate, pentaerythritol triacrylate, itaconic acid, maleic anhydride, maleic acid, esters and half esters, fumaric acid, esters and half esters, crotonic acid, etc.

Allyl Comonomers

Allyl diglycol carbonate, allyl alcohol, diallyl phthalate and isophthalate, allyl glycidyl ether, glyceryl allyl ether, allyl methacrylate and acrylate, triallyl cyanurate and isocyanurate, diallyl maleate, triallyl trimellitate, diallyl chlorendate, diallyl tetrabromophthalate, allyl ether of cyclic ureide, other diallyl fumarate, adipate, citrate, itaconate.

Halogenated Comonomers

Tetrafluoroethylene, vinylidene fluoride, vinyl fluoride, hexafluoropropylene, chlorotrifluoroethylene, perfluoropropyl vinyl ether, perfluoromethyl vinyl ether, perfluorosulfonyl ether, hexafluoropropylene oxide, etc.

Chlorine- or Bromine-containing Vinyl Comonomers

Vinyl chloride, vinyl bromide, vinyl benzyl chloride, vinyl chloroacetate, 2-chloroethyl vinyl ether, etc.

Quaternary Ammonium Comonomers

METAM(S)-quaternary product of dimethylamino ethyl methacrylate or diethylaminoethyl methacrylate and dimethyl sulfate.

METAM(Cl)-quaternary product of dimethyl- or diethyl-aminoethyl methacrylate and methyl chloride.

DADMAC-diallyldimethyl ammonium chloride, DADEAC-diallyldiethyl ammonium chloride, MAPTAC- a quaternary product of dimethyl- or diethyl-aminopropyl methacrylamide and methyl chloride; (3-methacrylamidopropyl)trimethyl ammonium chloride, multifunctional methacrylates such as ethylene glycol dimethacrylate, diethylene glycol dimethacrylate, tetraethylene glycol dimethacrylate, other polyethylene glycol dimethacrylates, butylene glycol dimethacrylate, trimethylolpropane trimethacrylate, ethoxylated bisphenol A dimethacrylate, etc.

Unsaturated Hydrocarbons Comonomers

Styrene, vinyl toluenes, alpha-methyl styrene, divinyl benzene, 1,4-hexadiene, ethylidene norbornene, other norbornene, 4-methyl pentene, ethylene, propylene, etc.

Macromonomers 2-polystyrylethyl methacrylate.

Vinyl Ester Comonomers

Vinyl acetate, vinyl versatate, vinyl crotonate, other propionate, laurate, etc., vinyl alkyl ethers, vinyl methyl ether, vinyl ethyl ether, isobutyl vinyl ether, divinyl ether, vinyl pyridines, N-vinyl pyrrolidone and N-vinylamides. The copolymer of the present monomer with vinyl acetate comonomer can be subsequently hydrolyzed to convert at least some of the ester groups to hydroxyl groups and provide a product having valuable properties.

Sulfonate Comonomers

Sodium styrene sulfonate, vinyl sulfonate, 2-sulfoethyl methacrylate, 2-acrylamido-2-methylsulfonic acid, etc.

Vinyl Ether Comonomers

Methyl vinyl ether, ethyl vinyl ether, butyl vinyl ether, etc.

The copolymers of the present invention may include one or more of the above comonomeric species.

It is found that the polymers of this invention form complexes having significantly higher stability than those formed with PVP. Also, the present polymers are capable of complexing with compounds such as the drug triamterene which is normally not complexible with other lactam polymers.

The present homopolymer complexes with iodine to form a more tightly bound product without reducing the quantity of iodine taken up by the polymer. The same effect is achieved with highly toxic drugs so that they are released into the system upon administration at a slower rate over a given period of time. Thus, complexing with the polymers of the present invention provides drugs in a less toxic form which are less irritating to the recipient and may even extend the time release of effective dosages.

Generally, the polymers of the present invention additionally possess hydrotropic properties; thus increasing the water solubility of many drugs and other organic compounds previously classified as water insoluble. For example, these complexes are useful as drug solubilizers when parenteral medicinal therapy requires dosages that are greater than the water solubility of the prescribed drug. Combinations of the new polymers or copolymers with such drugs may also change the rate at which the drug is absorbed and utilized in vivo, thereby making possible improved procedures of medication. Because of their hydrotropic properties, the polymers of the present invention can also be employed as additives for detergent formulations.

The monomeric compounds of the present invention are readily synthesized by a commercially feasible and economical process. In general, the process is effected by the reaction of a suitable lactam with acetylene or an aliphatically unsaturated ester or ether. The reaction can be represented by the following equations

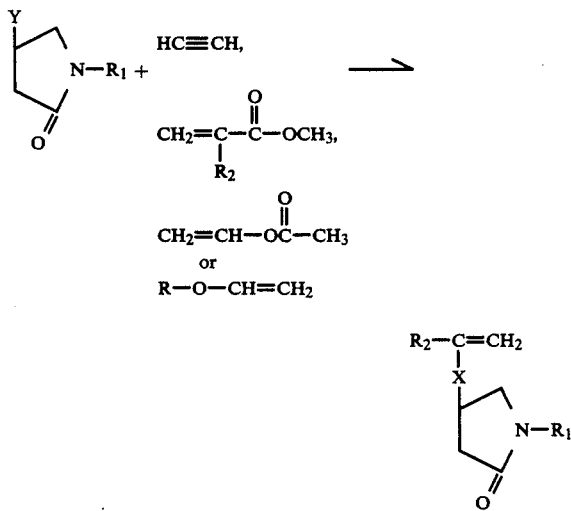

wherein Y is $-O-NH(R_3)$ $-CH_2OH$ or $COOH$ and $R_2$ and $R_3$ are each hydrogen or methyl, X is as defined above and R is a hydrocarbon radical having from 1 to 20 carbon atoms. The above reactions are carried out at a temperature of between 50° and about 250° C. under atmospheric pressure or pressures up to about 500 psig for a period of from about 2 to about 24 hours. Preferred reaction conditions include a temperature of between about 75° and about 180° C., under a pressure of from about 75 to about 225 psig for a period of from about 3 to about 16 hours. It is to be understood that under atmospheric conditions, the addition reaction with acetylene can be carried out without dilution of acetylene; however, at higher pressures the acetylene reactant is diluted with an inert gas such as propane, or nitrogen, up to about 50%.

In the reaction the mole ratio of the oxopyrrolidine reactant with coreactant is employed within the range of from about 1:5 to about 1:1, preferably from about 1:1.5 to about 1:1 when the coreactant is not used as a diluent for the process. The reactions with ester coreactant can range from about 1:1 to about 20:1, preferably from about 2:1 to about 5:1, with respect to lactam.

In general the above reactions are effected in the presence or absence of a catalyst. Suitable catalysts include dibutyl tin oxide, potassium butoxide, palladium chloride, mercuric acetate, the zinc salt of oxopyrrolidinecarboxylic acid, phenyl mercuric acetate, palladium chloride lithium nitrate, sodium palladium chloride or other suitable vinylation or transvinylation catalysts. When employed the amount of catalyst present in the system can range up to 40%, preferably between about 0.05 and about 10% based on the oxopyrrolidone reactant.

Although the reaction can be effected in the absence of a solvent, it is recommended that an inert liquid such as methylpyrrolidone, dimethylformamide, dimethylsulfoxide, dimethylacetamide or any other inert liquid medium be employed. When the reaction involves an acrylate coreactant an excess of this compound can serve as a diluent for the process. The reaction mixture may also contain a polymerization inhibitor when it is desirable to isolate the product in the monomeric state. Suitable inhibitors include benzoquinone, hydroquinone, nitrobenzene, aniline and phenothiazine which can be employed in an amount between about 0% and about 1% of the total reaction mixture. The product of the reaction is recovered by distillation at a temperature within the range of from about 110° to about 180° C. which can be carried out at atmospheric pressure or under vacuum as low as 0.1 mmHg. The overhead vapors are condensed and recovered as the liquid product of the process. Reactions with acetylene are effected in our oxygen free atmosphere and require an alkali metal, zinc or cadmium catalyst. In this reaction, the catalyst is employed in a concentration of from about 0.5% to about 10% based on lactam reactant.

The oxopyrrolidine derivative obtained as described above can be homopolymerized or copolymerized with any of the aforementioned comonomers, which reaction is generally effected in the presence of an initiator such as 2,2'-azobis(2-methylpropane nitrile), t-butylperoxypivalate, benzoyl peroxide, t-butylperoxide, t-butylhydroperoxide, etc. In general, the polymerizations of the present invention are carried out at a temperature between about 50° C. and 100° C. under atmospheric pressure for a period of from about 10 hours to about 3 days, after which the product is dissolved in a suitable inert solvent such as t-butanol, methanol, ethanol isopropanol, etc., precipitated in a non-solvent eg. an ether or saturated hydrocarbon and collected as a product of the process. Preferred polymerization conditions include a temperature of between about 60° C. and about 85° C. for a period of from about 10 to about 80 hours. Although not required, the polymerization reactions are generally carried out in the presence of an inert solvent such as water, t-butanol, benzene, dimethylformamide, etc. The use of a solvent provides better control of reaction conditions and molecular weight of the polymeric product. Polymers of the present products can be prepared by condensation, e.g. by reacting polyvinyl alcohol with a pyrrolidone carboxylic acid, i.e.

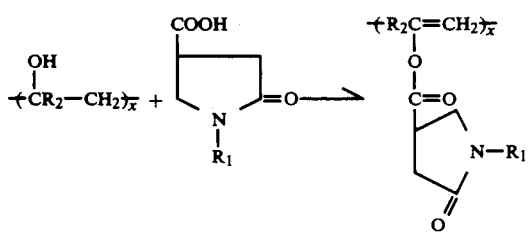

or by reacting a polymethacrylic acid with hydroxymethyl pyrrolidone, i.e.

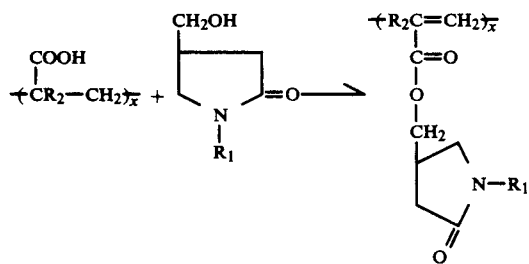

The polymers of this invention have a number average molecular weight ranging between about 1,600 and about 8,500,000, preferably within the range of 25,000 and 100,000 depending on the solvent, catalyst, and reaction temperature and time.

The polymeric products of this invention present many complexing sites which are free from steric hindrance, consequently, they form complexes with a wide variety of drugs including nonphenolics such as indomethacian and other indole type compounds which are highly insoluble in water. They also complex with phenolic and other compounds having an acidic hydrogen to provide highly stable products. The insoluble compounds are rendered water soluble through the formation of complexes with the present polymers and toxic compounds, in the complexed form, become less irritating.

Having thus generally described the invention, reference is now had to the accompanying examples which set forth preferred embodiments but which are not to be construed as limiting to the scope of the invention as more broadly defined above and in the appended claims.

EXAMPLE I

Preparation of the Oxopyrrolidinecarboxylic Zinc Salt Catalyst

Into a 1-liter, 4 necked round bottom flask fitted with an overhead stirrer, thermometer, Dean Stark Trap, condenser, drying tube and heating mantle with transformer, containing 200 grams of N-methyl pyrrolidone and 400 ml. of toluene, at 95° C. was added 172 grams of 1-methyl-5-oxo-3-pyrrolidinecarboxylic acid. After the acid had dissolved, 46.4 grams of zinc oxide were added and the mixture heated at reflux while the water was removed azeotropically. The mixture was then filtered and the precipitate washed with 600 ml. of toluene.

The solid precipitate was returned to the apparatus, 600 ml. of toluene added, and the mixture again subjected to azeotropic distillation. Since less than 0.2 ml. of water was collected, the mixture was found to be substantially anhydrous. The solid product was filtered and the white precipitate placed in a vacuum oven and dried overnight in vacuo at 90° C. The dried zinc salt product weighed 190 grams.

EXAMPLE II

Into a nitrogen purged 1-liter pressure reactor at 140° C. containing 250 grams of 1-methyl-5-oxo-3-pyrrolidinecarboxylic acid, 75 grams of the zinc salt catalyst as prepared in Example I, and 250 grams of N-methylpyrrolidone solvent, acetylene gas was introduced until the pressure reached 100 psig. The temperature of the reaction mixture, after 3 hours, was raised to 150° C. for 3 hours. and then raised to 160° C. for an additional 3 hours. The reactor was then cooled to room temperature the autoclave vented and purged with nitrogen.

The contents were transferred to a larger container and 1 liter of ethyl acetate was added to precipitate the catalyst. After filtration and washing with ethyl acetate, the solid precipitate can be dried in vacuo and used as catalyst for subsequent vinylation reactions with acetylene.

The filtrate and washings were stripped of ethyl acetate and the residue distilled in vacuo. The fraction boiling at 149°-160° C. at 2.2 mm. of mercury pressure, weighed 69 grams and was indentified as the vinyl ester of 1-methyl-5-oxo-3-pyrrolidinecarboxylic acid.

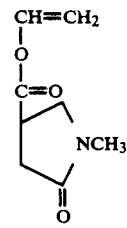

EXAMPLE III

Into a nitrogen purged, one gallon autoclave at 160° C. containing 775 grams of N-methyl-2-pyrrolidone solvent 775 grams of 1-methyl-5-oxo-3-pyrrolidinecarboxylic acid and 775 grams of the zinc salt catalyst as prepared in Example I, propane gas was introduced until the pressure reached 100 psig after which acetylene gas was introduced until a pressure of 200 psig was attained. The temperature and pressure of the reaction mixture was maintained for 10 hours, after which the reactor contents was divided and transferred to 2 one gallon jars.

The jars were then filled with ethyl acetate to precipitate the catalyst which was removed. The ethyl acetate washing was repeated, the resulting precipitate removed and the filtrates combined.

The combined filtrates were stripped of ethyl acetate, distilled in vacuo to remove N-methyl pyrrolidone and cooled. Ethyl acetate (600 ml) was then added to precipitate unreacted acid, the mixture was filtered, the filtrate was stripped of ethyl acetate and the remaining liquid distilled in vacuo. The fraction boiling at 122°-125° C. at 0.5 mm. of mercury pressure, weighed 319 grams and was indentified by IR Spectrum, proton magnetic resonance and C-13 magnetic resonance as the vinyl ester of 1-methyl-5-oxo-3-pyrrolidinecarboxylic acid.

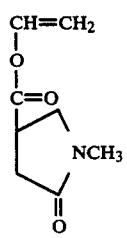

The above Examples II and III are repeated except that other species of oxo-pyrrolidinecarboxylic acids are substituted as reactants in the process. For example, 1-octyl-5-oxo-3-pyrrolidinecarboxylic acid produces

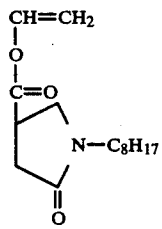

in good yield; 1-butyl-5-oxo-3pyrrolidinecarboxylic acid produces

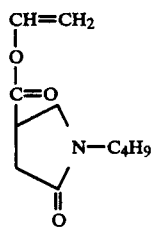

in good yield and 1-phenyl-5-oxo-3-pyrrolidinecarboxylic acid produces

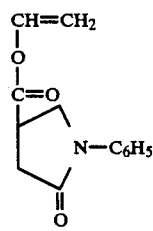

EXAMPLE IV

A 1-liter 4-necked round bottom flask was fitted with a condenser, thermometer and mechanical stirrer, and charged with 87.5 grams of (1-methyl-5-oxo-3-pyrrolidinyl) methyl alcohol, 636 grams of methyl methacrylate, 2.4 grams of dibutyltin oxide catalyst, and 1.1 grams of hydroquinone. The contents of the flask were heated at slow reflux temperature for 3–5 hours while the by-product methanol was continuously azeotropically distilled off with unreacted methyl methacrylate. The reaction was monitored by gas chromatography (GC). When methanol was completely distilled off, the residue was stripped of excess methyl methacrylate and then distilled at reduced pressure. The fraction boiling at 140° C. and 1 mm. of mercury pressure (55 grams) was collected and identified by IR spectrum, proton magnetic resonance and C-13 magnetic resonance as r(1-methyl-5-oxo-3-pyrrolidinyl) methyl] methacrylate

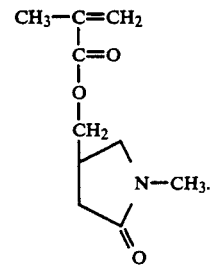

EXAMPLE V

A 100 ml. round bottom flask fitted with a Dean Starke Trap and a mechanical stirrer was charged with 10.1 grams of [(1-methyl-5-oxo-3-pyrrolidinyl)] methyl alcohol, 64 grams of methyl acrylate, 0.27 grams of dibutyltin oxide and 0.13 grams of hydroquinone. The mixture was heated gradually at a temperature of between 75° C. and 85° C. for continuous removal of by-product methanol over a period of about 6 hours. Equal volumes of water, and dichloromethane were then added and the mixture partitioned. The dichloromethane layer was drawn off, and the remaining product dried over magnesium sulfate, filtered, and the solvent stripped. The residue was dried under vacuum overnight and it was identified as [(1-methyl-5-oxo-3-pyrrolidinyl) methyl] acrylate,

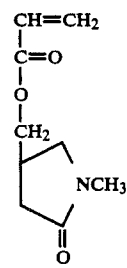

Examples IV and V wherein other species of (5-oxo-3-pyrrolidinyl)methyl] alcohol are substituted can be repeated. For example [(1-octyl-5-oxo-3-pyrrolidinyl) methyl]alcohol, [(1-butenyl-5-oxo-3-pyrrolidinyl).-]methyl alcohol etc. can be substituted to provide the corresponding methacrylate or acrylate derivatives in good yield.

EXAMPLE VI

A 1-liter autoclave was charged with 100 grams of 1,N-dimethyl-5-oxo-3-pyrrolidinecarboxamide, 3 grams of potassium butoxide, and 250 grams of N-methylpyrrolidone. The autoclave was purged with nitrogen, heated to 160° C., and acetylene added to a pressure of 100 psig. After 8.5 hours at 160° C. and 100 psig, the reactor was cooled to room temperature, was vented and the remainder was purged with nitrogen.

The 1,N-dimethyl-N-vinyl-5-oxo-3-pyrrolidine carboxamide product,

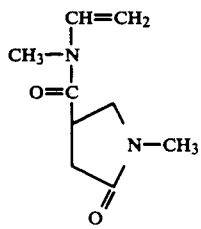

obtained in 10% yield, was identified by GC and Mass Spectroscopy.

EXAMPLE VII

Into a 500 ml round bottom 3-necked flask, equipped with a nitrogen inlet, condenser, gylcerine bubbler, thermometer, stirring bar and heating mantle was added 106 g. of vinyl acetate, 57 g. of 1-methyl-5-oxo-3-pyrrolidine carboxylic acid, 50 ml of N-methylpyrrolidone, 1.136 g. of mercury acetate and 0.138 g. of 100% sulfuric acid. The system was purged with nitrogen stirred and heated at reflux for 16 hours. Transvinylation occurred and the product

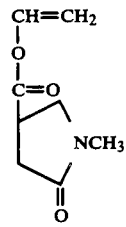

was recovered.

EXAMPLE VIII

Into a one liter round bottom 3 necked flask similarly equipped as described in Example VII, was added 400 g. of vinyl acetate, 150 g. of 1-methyl-5-oxy-3-pyrrolidine carboxylic acid, 200 ml of N-methylpyrrolidone, 2.784 g. of PdCl$_2$, 0.666 g. of lithium chloride and 0.2 g. of hydroquinone. The mixture was stirred, heated at reflux for 15 hours and then cooled and subjected to fractional distillation. Twenty seven grams of product in 87% purity was collected.

EXAMPLE IX

Homopolymerization of Vinyl 1-Methyl-5-Oxo-3-Pyrrolidinecarboxylate

A polymerization tube was charged with 20 grams of vinyl 1-methyl-5-oxo-3-pyrrolidinecarboxylate and 0.2 grams of 2,2'-azobis (2-methylpropanenitrile) (polymerization initiator).

The tube was degassed with nitrogen for 30 minutes, evacuated, sealed and placed in an oil bath for 3 days at 67° C. The reactor tube was unsealed, the crude product was dissolved in 60 ml of t-butanol and the solution poured into 1-liter of diethyl ether. The precipitated polymer was filtered off and dried in dynamic vacuum in a desiccator containingphosphorus pentoxide. About 20 grams of the dried polymer

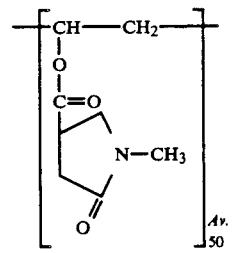

was recovered. A 1% aqueous solution of the product had a relative viscosity of 1.166 at 25° C. The polymer structure was verified by C-13 and proton magnetic resonance.

EXAMPLE X

Copolymerization of Vinyl 1-methyl-5-oxo-3-pyrrolidinecarboxylate (VMOP) with vinyl acetate (VA)

The properties of the copolymer depend on the ratio of the two monomers used in the copolymerization reaction. This is illustrated by the data of seven copolymers prepared simultaneously by the following procedure.

The two monomers were weighed into each of seven 4 ounce narrow-mouth bottles. Into each bottle was introduced 50 grams of t-butanol and 0.3 grams of 2,2'-azobis(2-methylpropanenitrile) (Vazo 64).

Each bottle was covered with a rubber septum having a gas inlet and outlet and degassed with nitrogen gas for 20 minutes. The inlet and outlet were removed and the bottles were shaken until all Vazo 64 dissolved.

The bottles were then placed in an oil bath at 70° C. overnight, and the copolymers were precipitated by addition to a non-solvent noted in Table II and isolated by filtration. The recovered products were dried overnight in vacuum.

The results of these experiments are tabulated in Tables I, II, and III.

TABLE I

| Copolymer Number | Grams VA | Grams VMOP | % VA | % VMOP |
|---|---|---|---|---|
| 1 | 1.5 | 28.5 | 5 | 95 |
| 2 | 3.0 | 27.0 | 10 | 90 |
| 3 | 7.5 | 22.5 | 25 | 75 |
| 4 | 15.0 | 15.0 | 50 | 50 |
| 5 | 22.5 | 7.5 | 75 | 25 |
| 6 | 27.0 | 3.0 | 90 | 10 |
| 7 | 28.5 | 1.5 | 95 | 5 |

TABLE II

| Copolymer Number | Precipitating Non-Solvent | Drying Temperature |
|---|---|---|
| 1 | 600 ml. ethyl ether | 60° C. |
| 2 | 600 ml. ethyl ether | 60° C. |
| 3 | 600 ml. ethyl ether | 60° C. |
| 4 | 600 ml. ethyl ether, + 60 ml. cyclohexane | 80° C. |
| 5 | 600 ml. cyclohexane | 80° C. |
| 6 | 600 ml. isopropanol | 80° C. |
| 7 | 600 ml. isopropanol | 80° C. |

All dried copolymeric products weighed about 30 grams.

TABLE III

| Copolymer Number | Aqueous Solution Appearance | Aqueous Solution Relative Viscosity | Methanolic Solution Appearance | Methanolic Solution Relative Viscosity |
|---|---|---|---|---|
| 1 | Clear | 1.12 | — | — |
| 2 | Clear | 1.10 | — | — |
| 3 | Clear | 1.11 | — | — |
| 4 | Cloudy | 1.04 | Clear | 1.16 |
| 5 | Insoluble | — | Clear | 1.23 |
| 6 | Insoluble | — | Clear | 1.31 |
| 7 | Insoluble | — | Clear | 1.34 |

Properties of 1% solutions at 25° C.

EXAMPLE XI

Homopolymerization of [(1-Methyl-5-Oxo-3-Pyrrolidineyl)methyl] Methacrylate

A 250 ml. round bottom 3-necked flask fitted with condenser, mechanical stirrer and thermometer was charged with 15 grams of [(1-methyl-5-oxo-3-pyrrolidinyl)methyl]methacrylate, and 40 grams of benzene solvent. The solution was purged for 30 minutes at 60° C. with nitrogen gas, after which 0.15 grams of t-butylperoxy pivalate polymerization initiator was added and the mixture heated at 60° C. for 16 hours, with constant stirring.

The contents were stripped of solvent and the residue dried in vacuum for 2 days. The polymer weighed 15 grams and was identified as poly[(l-methyl-5-oxo-3-pyrrolidinyl)methyl] methacrylate

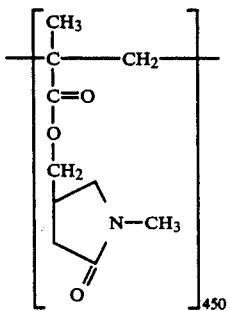

by gel permeation and proton magnetic resonance.

EXAMPLE XII

Example XI was repeated except that 40 grams of water solvent was substituted for benzene. The same polymeric product was recovered.

EXAMPLE XIII

Example XI was repeated except that 40 grams of dimethylformamide solvent was substituted for benzene. Again, the same polymeric product was recovered.

EXAMPLE XIV

Homopolymerization of [(1-Methyl-5-Oxo-3-Pyrrolidinyl)methyl] Acrylate

A 250 ml. 3-necked round bottom flask fitted with thermometer, condenser, and magnetic stirrer was charged with 8.5 grams of [(1-methyl-5-oxo-3-pyrrolidinyl)methyl]acrylate and 27 grams of dimethylformamide solvent added. The solution was purged with nitrogen gas for 30 minutes and 0.085 grams of t-butylperoxy pivalate polymerization initiator added, and the mixture stirred at 60° C. for 70 hours. The reactor contents was stripped of solvent and the residue dried in vacuum. The polymeric homopolymer weighed about 8.5 grams, and was identified as poly(1-methyl-5-oxo-3-pyrrolidinyl)methyl] acrylate

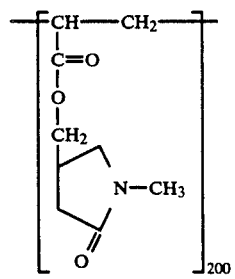

by gel permeation and proton magnetic resonance.

EXAMPLE XV

Copolymerization of L(l-Methyl-5-Oxo-3-Pyrrolidinyl)methyl] Methacrylate and Vinyl Pyrrolidone A 250 ml. round bottom 3-necked flask fitted with condenser, magnetic stirrer, thermometer, and dropping funnel was charged with 75 grams of vinyl pyrrolidone and 80 grams of deionized water solvent. The solution was heated to 60° C. and purged with nitrogen gas for 30 minutes. Then 0.75 grams of t-butylperoxy pivalate was added in one portion and 7.5 grams of [(1-methyl-5-oxo-3-pyrrolidinyl)methyl] methacrylate suspended in 20 grams of deionized water added slowly from the dropping funnel over a period of 1 hour. The mixture was stirred continuously for 70 hours at 60° C., after which an additional 0.5 grams of t-butylperoxy pivalate was added, and the mixture stirred for an additional 14 hours.

After cooling, water was removed by freeze drying.

Any of the other aformentioned comonomers can be substituted in Examples X or XV to provide the corresponding copolymers in good yield.

EXAMPLE XVI

An 8 ounce jar was charged with 1.33 grams of iodine, 0.873 grams of potassium iodide, and 10 grams of poly(vinyl 1-methyl-5-oxo-3-pyrrolidinecarboxylate) as prepared in Example IX. The jar was labeled PVMOP.

A second jar was charged with 1.33 grams of iodine, 0.873 grams of potassium iodide, and 10 grams of polyvinylpyrrolidone. This jar was labeled PVP.

Water was added to each jar to bring the total weight of the contents in each jar up to 100 grams. The two mixtures were stirred overnight. From each jar, two samples of 20.83 grams each were pipetted and each of the 4 samples labeled as to origin.

Each sample was then diluted with water to a weight of 25 grams and 2 duplicate 1 ml. aliquots were pipetted from each sample for analysis and coded A and B.

Each of the eight 1 ml. aliquots was added to 25.0 ml. of water saturated heptane and the mixtures agitated vigorously for 2 minutes the resulting two phases were permitted to separate and the heptane layer was withdrawn. The iodine absorbance of the heptane phase was measured at 515 nm against the water saturated heptane references as reported in the following Table IV.

TABLE IV

| POLYMER/SAMPLE | | ABSORBANCE | |
|---|---|---|---|
| PVP | 1A | 0.140 | AVERAGE 0.143 |
| | 1B | 0.138 | |
| | 2A | 0.148 | |
| | 2B | 0.145 | |
| PVMOP | 1A | 0.068 | AVERAGE 0.074 |
| | 1B | 0.072 | |
| | 2A | 0.078 | |
| | 2B | 0.077 | |

The results indicate that PVMOP has a significantly greater affinity for iodine than that of polyvinylpyrrolidone.

EXAMPLE XVII

Indomethacin is an anti-inflammatory drug whose solubility in water does not exceed 5 ppm at room temperature. A phosphate buffer solution was prepared by diluting 4.588 g. of dibasic potassium phosphate and 2.722 g. of monobasic potassium phosphate to a 1 liter volume with distilled water.

To a 40 wt % aqueous solution of poly(vinyl 1-methyl-5-oxo-3-pyrrolidinecarboxylate) of Example IX with the phosphate buffer at pH 6.95 was added sufficient indomethacin to bring its concentration in the mixture up to 5000 ppm, about 1000 times its water solubility, at room temperature.

The mixture was agitated for 90 minutes at 85° C. and then cooled to room temperature. The solution remained perfectly clear, there being no sign of insoluble material. The solution remained clear for one week, after which it was discarded. The polymer increased the water solubility of the drug at least a thousand fold.

The above experiment was repeated for each of aspirin, acetaminophen and piroxicam in place of indomethacin. In each case clear solutions were obtained and remained clear for one week before they were discarded.

It is to be understood that many alterations and modifications can be made in the above examples without departing from the scope of this invention. For example, higher molecular weight polymers and copolymers can be prepared by changing conditions of polymerization such as initiator, temperature and solvent. Also homopolymers and copolymers of any of the present pyrrolidone monomer species can be prepared by substitutions in Examples IX through XV to provide polymeric products having the beneficial properties indicated above.

EXAMPLE XVIII

Triamterene has previously been found insoluble in aqueous solutions of polymers containing lactam rings and is generally administered in tablet or powder form. The procedure of Example XVII was repeated on Triamterene, except that 50 wt % of phosphate buffered aqueous solution, i.e. poly(vinyl 1-methyl-5-oxo-3-pyrrolidinecarboxylate) was employed. After cooling, a stable transparent gel was obtained. The same stable transparent gel was achieved when the concentration of triamterene was increased to 0.75% and to 1% which indicated that some solubilization of the drug resulted.

When the procedure of Example XVII was repeated with vinylpyrrolidone polymers; (C15 M.W.no.av. ∼ 5,000 and C30 M.W.no.av. ∼ 10,000), the drug immediately precipitated since it was totally insoluble in these aqueous solutions.

What is claimed is:

1. A homopolymer having the formula

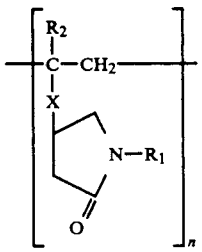

wherein n has a value of from 10 to 50,000 $R_2$ is H or $CH_3$, $R_1$ is H or a hydrocarbon radical having from 1 to 20 carbon atoms, X is selected from the group of

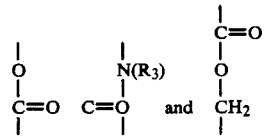

where $R_3$ is hydrogen or methyl.

2. The homopolymer of claim 1 wherein $R_1$ is hydrogen or lower alkyl.

3. The hompolymer of claim 2 wherein X is

4. The hompolymer of claim 2 wherein X is

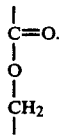

5. The hompolymer of claim 2 wherein X is

6. The hompolymer of claim 2 wherein X is

7. The complex of iodine and the hompolymer of claim 1.

8. The complex of claim 7 wherein X is

17
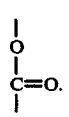
* * * * *
18
* * * * *